(12) United States Patent  
Jones et al.

(10) Patent No.: US 7,712,360 B2  
(45) Date of Patent: May 11, 2010

(54) AIR SEPARATOR FOR OPHTHALMIC SURGICAL SYSTEM

(75) Inventors: Ross Peter Jones, Cambridge (GB); Mark Ian Lutwyche, Reisterstown, MD (US)

(73) Assignee: Bausch & Lomb Incorporated, Rochester, NY (US)

( * ) Notice: Subject to any disclaimer, the term of this patent is extended or adjusted under 35 U.S.C. 154(b) by 192 days.

(21) Appl. No.: 11/955,638

(22) Filed: Dec. 13, 2007

(65) Prior Publication Data

US 2009/0157018 A1   Jun. 18, 2009

(51) Int. Cl.  
*G01F 15/08* (2006.01)  
*A61M 1/00* (2006.01)

(52) U.S. Cl. ........................ 73/200; 604/317  
(58) Field of Classification Search .................. 73/200; 604/317–319  
See application file for complete search history.

(56) References Cited

U.S. PATENT DOCUMENTS

| | | | |
|---|---|---|---|
| 3,347,096 A * | 10/1967 | Person | 73/200 |
| 4,295,260 A | 10/1981 | Divers | |
| 4,688,418 A * | 8/1987 | Cheung et al. | 73/29.01 |
| 4,760,742 A * | 8/1988 | Hatton | 73/861.04 |
| 5,127,272 A * | 7/1992 | Dean et al. | 73/861.04 |
| 5,390,547 A * | 2/1995 | Liu | 73/861.04 |
| 5,441,482 A | 8/1995 | Clague | |
| 5,483,830 A * | 1/1996 | Dietz et al. | 73/226 |
| 5,526,684 A * | 6/1996 | Liu et al. | 73/200 |
| 6,599,277 B2 | 7/2003 | Neubert | 604/317 |
| 6,634,237 B2 | 10/2003 | Neubert | 73/861.12 |
| 6,984,260 B2 * | 1/2006 | Atkinson et al. | 96/188 |
| 7,469,727 B2 * | 12/2008 | Marshall | 141/65 |
| 2007/0219493 A1 | 9/2007 | Domash | 604/122 |
| 2007/0219494 A1 | 9/2007 | Gao et al. | 604/122 |
| 2009/0158812 A1 * | 6/2009 | Jones | 73/19.1 |

FOREIGN PATENT DOCUMENTS

EP   1535641 A   6/2005

OTHER PUBLICATIONS

International Search Report (PCTISA/210) and Written Opinion (PCT/ISA/237) mailed on Aug. 6, 2009.

* cited by examiner

*Primary Examiner*—Harshad Patel  
(74) *Attorney, Agent, or Firm*—Jeffrey B. Powers

(57) ABSTRACT

An air bubble separator is provided for ophthalmic surgical systems, which includes a housing 102 having a diagonally-oriented flow channel 110 and a vertically-oriented flow channel 130 adjoining the diagonally oriented channel. The diagonally-oriented flow channel 110 has a downstream portion 112 disposed downstream of the vertically-oriented flow channel 130, and an upstream portion 118 disposed upstream of the vertically-oriented flow channel 130. The downstream portion 112 of the diagonally-oriented flow channel 110 has a cross-sectional area 114 that is greater than that of the upstream portion 118. The downstream portion's cross-sectional area 114 is greater than the upstream portion's cross-sectional area 124 by an amount or percentage that is sufficient to slow fluid flow through the diagonally-oriented flow channel 110, so as to cause air within the fluid to rise and flow into the vertically-oriented flow channel 130.

18 Claims, 2 Drawing Sheets

AIR SEPARATOR FOR OPHTHALMIC SURGICAL SYSTEM

FIELD

The present invention relates to sensing an aspiration flow rate in a surgical pump system. More particularly, the present application is directed towards cassettes for use with ophthalmic microsurgical pump systems.

BACKGROUND

The statements in this section merely provide background information related to the present disclosure and may not constitute prior art.

The flow and flow rate of tissue and fluids through an aspiration tube is of interest during operations, including ophthalmic operations. During ophthalmic microsurgery, small probes are inserted into an operative site to remove tissues and fluids may be infused into the operative site. Infusion fluids may also be aspirated from the site. Surgical cassettes may also be coupled to surgical probes, to provide for collection of aspirated fluids. Measurement of the surgical aspiration flow rate may be valuable in that it can provide for safe control of the ophthalmic surgical equipment. However, passage of air bubbles, among other factors, within the aspiration measurement device can make measurement of the flow rate difficult to achieve.

Therefore, it would be desirable to incorporate an air filtering or diverting means into a disposable surgical cassette to permit accurate measurement of flow rate by removing or greatly reducing any effect of the air bubbles.

SUMMARY

The present disclosure relates to ophthalmic surgical systems in which an aspiration flow channel is disposed and configured to separate air from liquid flowing therethrough. In accordance with one aspect of the present application, a surgical cassette for ophthalmic surgical systems is provided that includes a housing that has a first diagonally-oriented flow channel and a second vertically-oriented flow channel adjoining the first diagonally-oriented flow channel to establish fluid communication therebetween. The first diagonally-oriented flow channel has a downstream portion disposed downstream of the second vertically-oriented flow channel, and an upstream portion disposed upstream of the second vertically-oriented flow channel. The downstream portion of the first diagonally-oriented flow channel has a cross-sectional area that is greater than that of the upstream portion. The downstream portion's cross-sectional area is greater than the upstream portion's cross-sectional area by an amount or percentage that is sufficient to slow fluid flow through the first diagonally-oriented flow channel, so as to allow air within the fluid to rise and flow into the second vertically-oriented flow channel.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

DETAILED DESCRIPTION

Figure 1:
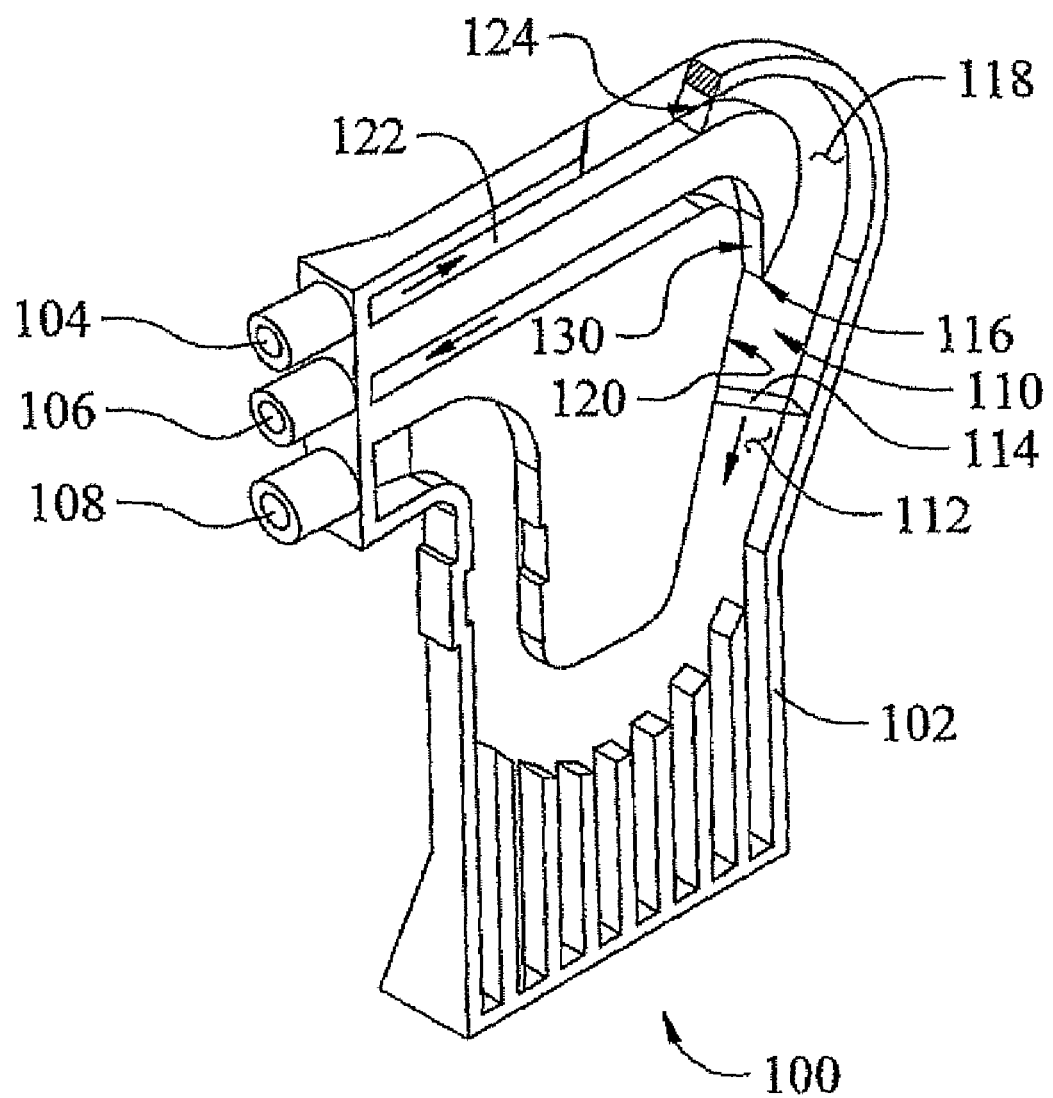
FIG. 1 is a cut-away perspective view of part of a housing for one embodiment of a cassette for an ophthalmic surgical system in accordance with the principles of the present disclosure.

The following description is merely exemplary in nature and is not intended to limit the present disclosure, application, or uses. It should be understood that throughout the drawings, corresponding reference numerals indicate like or corresponding parts and features.

In one embodiment, an air separator is provided in a aspiration flow measurement device 100 for use in ophthalmic surgical systems. The aspiration flow measurement device 100 includes a housing 102 that may have an inlet 104 for receiving an aspirated fluid from a surgical site (not shown), an outlet 106 for output of air separated from the aspirated fluid, and an outlet 108 for output of the aspirated fluid to a collection reservoir (not shown). The housing 102 has a diagonally-oriented flow channel 110, and a vertically-oriented flow channel 130 that adjoins the diagonally-oriented flow channel at a junction 116.

The diagonally-oriented flow channel 110 has a downstream portion 112 disposed downstream of the junction 116. The diagonally-oriented flow channel 110 also has an upstream portion 118 disposed upstream of the junction 116, which is in communication with an inlet flow channel 122. The inlet flow channel 122 (and the inlet to the upstream portion 118) has a cross-sectional area 124 of a size that is sufficient to permit or establish a fluid flow velocity $V_f$ of, for example, between 100 and 130 millimeters per second therethrough. The downstream portion 112 of the diagonally-oriented flow channel 110 has a cross-sectional area 114 that is greater than that of the upstream cross-sectional area 124. Preferably, the downstream portion's cross-sectional area 114 is greater than the upstream cross-sectional area 124 by an amount or percentage that is sufficient to slow fluid flow through the diagonally-oriented flow channel 110 so as to cause air within the fluid to rise along the diagonally-oriented surface 120 and enter into the vertically-oriented flow channel 130. Of course, those skilled in the art will realize that diagonally-oriented flow channel 110 could also be vertically-oriented. Therefore, the use of the term "diagonally-oriented" should also be understood to include vertically-oriented.

Specifically, the downstream cross-sectional area 114 is greater by an amount or percentage that is effective to increase resistance to flow and reduce the velocity of flow in the downstream portion to an extent that the buoyancy of any air causes the air to rise at a velocity faster than the velocity of the fluid flowing through the downstream portion. Thus, the downstream cross-sectional area 114 is greater than the upstream cross-sectional area 124 by an amount or percentage that will reduce the flow velocity of fluid in the downstream portion 112 to a velocity that is about the same as or less than the velocity of air bubbles rising due to buoyancy in the downstream portion 112.

It should be noted that in the embodiment shown in FIG. 1, the upstream cross-sectional area 124 is not disposed immediately preceding the junction 116, but rather is positioned at a distance upstream of the junction 116, as shown in FIG. 1. However, the upstream cross-sectional area 124 may be disposed closer to the junction 116. More specifically, the upstream cross-sectional area 124 is preferably within a predetermined distance of the junction 116, such that fluid flow velocity through the upstream cross-sectional area 124 is subsequently slowed to a separation velocity $V_S$ at a point downstream of the junction 116 between the diagonally-oriented flow channel 110 and the vertically-oriented flow channel 130. This predetermined distance ensures that air bubbles will begin rising (or establish a velocity in an upward direction) after they have moved downstream of the junction 116, such that the bubbles will rise upward into the vertically-oriented flow channel 130. It should be noted that the upstream portion 118 may vary in cross-section to provide a gradual transition between the upstream cross-sectional area 124 and the downstream cross-sectional area 114. The transition from the upstream cross-sectional area 124 likewise is within a predetermined distance of the junction 116, to thereby ensure that that air within the fluid will have passed downstream of the junction 116 before rising upward towards the vertically-oriented flow channel 130. While the upstream cross-sectional area 124 shown in FIG. 1 is disposed a distance upstream of the junction 116, the upstream cross-sectional area 124 may be positioned closer to the junction 116, as in the second embodiment of an air separator shown in FIG. 2.

Figure 2:
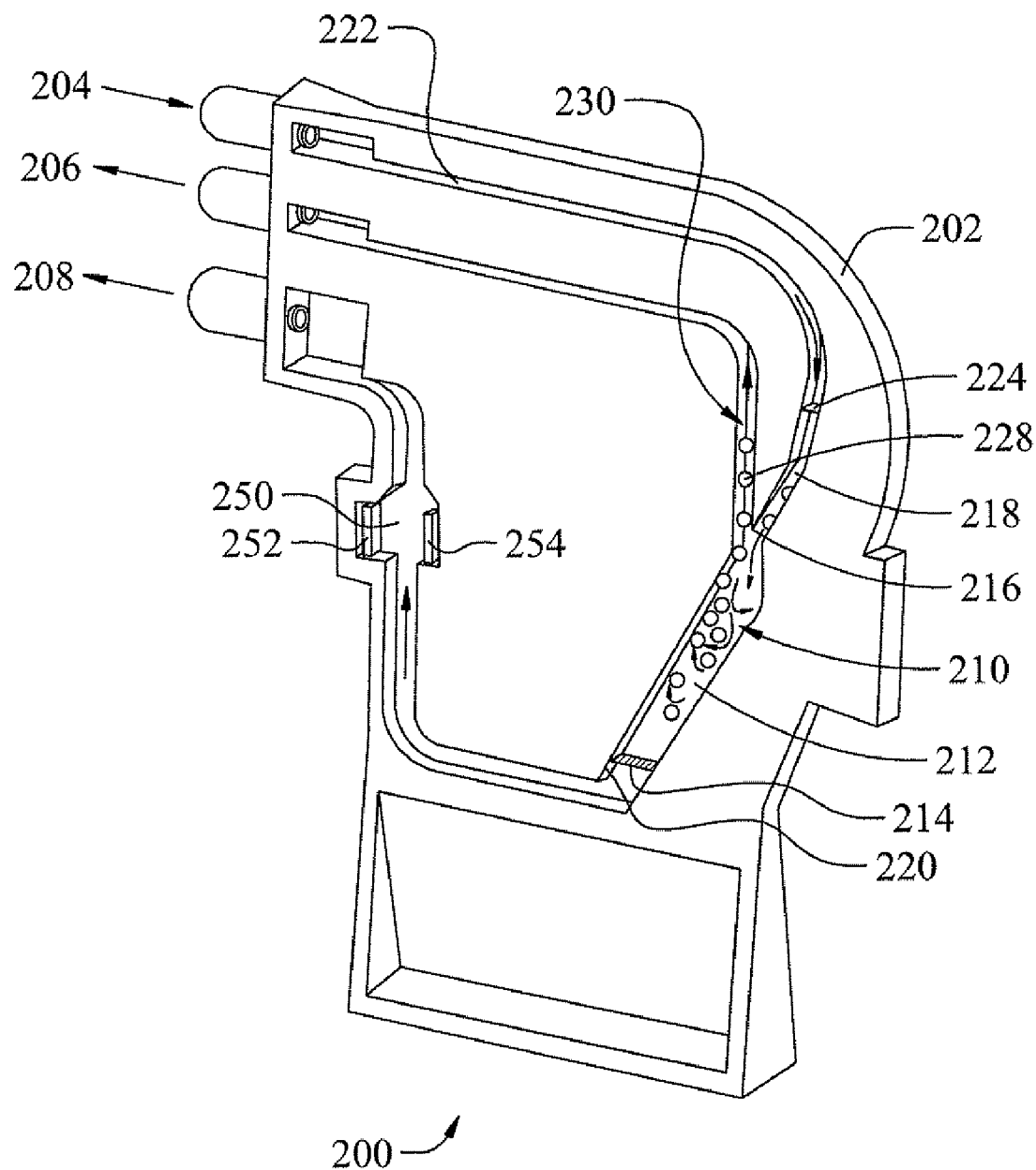
FIG. 2 is a cut-away perspective view of part of a housing for a second embodiment in accordance with the principles of the present disclosure.

Referring to FIG. 2, a second embodiment of an air separator within a flow measurement device 200 for use in ophthalmic surgical systems is provided with an inlet 204 and outlets 206 and 208, similar to inlet 104 and outlets 106 and 108 of FIG. 1. The flow measurement device 200 includes a housing 202 that includes a diagonally-oriented flow channel 210 and a vertically-oriented flow channel 230 that adjoins the diagonally-oriented flow channel at a junction 216. The diagonally-oriented flow channel 210 has an upstream portion 218 disposed upstream of the junction 216, and a downstream portion 212 disposed downstream of the junction 216. The diagonally-oriented flow channel 210 also has an upstream portion 218 that is in communication with an inlet flow channel 222. The upstream portion 218 includes an upstream cross-sectional area 224 of a size that is sufficient to permit or establish a fluid flow velocity $V_f$ of, for example, between 100 and 130 millimeters per second therethrough. The downstream portion 212 has a cross-sectional area 214 that is greater than that of the upstream cross-sectional area 224. In this second embodiment the upstream cross-sectional area 224 is disposed immediately upstream of the junction 216, as shown in FIG. 2. As in the first embodiment, the upstream cross-sectional area 224 and the transition region are disposed within a predetermined distance of the junction 216 of the vertically-oriented flow channel 230. The downstream portion's cross-sectional area 214 is greater than that of the upstream cross-sectional area 224 by an amount that is sufficient to slow fluid flow through the flow channel 210 as it passes the junction 216 so as to allow air within the fluid flow to rise along the first diagonally extending surface 220 and into the generally vertical flow channel 230. Likewise, the upstream cross-sectional area 224 is preferably within a predetermined distance of the junction 216, such that fluid flow velocity through the upstream cross-sectional area 224 is subsequently slowed to a separation velocity $V_S$ at point downstream of the junction 216 between the diagonally-oriented flow channel 210 and the vertically-oriented flow channel 230. This predetermined distance ensures that air bubbles 228 within the fluid will begin rising (or establish a velocity in an upward direction) after passing downstream of the junction 216, such that the air bubbles 228 will rise upward into the vertically-oriented flow channel 230.

In the second embodiment, the housing 202 further includes an electrode chamber 250 for measuring aspiration fluid flow rate. The fluid measurement means preferably utilizes an isolated Hall-effect electromagnetic flow meter (not shown, but described in U.S. Pat. Nos. 6,599,277 and 6,634,237), which takes advantage of the fact that the saline solution commonly used in ophthalmic surgery is electrically conductive. The Hall-effect involves the development of a voltage potential across conductive fluids flowing between current-carrying conductors 252 and 254, when subjected to a magnetic field. Thus, a voltage can be induced across an aspiration collection reservoir if a magnetic field is applied. Such flow measurement in an ophthalmic surgical pump system includes the application of a magnetic field source or electromagnetic magnet. The flow sensing electrode chamber 250 further includes first and second electrode terminals 252 and 254 disposed on generally opposite sides of the electrode terminal chamber 250. The fluid flowing through the electrode terminal chamber 250 generally comprises an electrically conductive saline solution. Accordingly, the first and second electrode terminals 252 and 254 are arranged opposite one another in a spaced-apart relationship that is sufficient to generate at least one electrical signal indicative of the flow rate of the fluid flowing through the electrode terminal chamber 250. Thus, the flow channels 210 and 230 are configured to separate air from the stream of fluid flow prior to fluid flow reaching flow sensing electrode chamber 250, to thereby allow a measurement of fluid flow without interference from noise inducing air bubbles. A similar arrangement is also embodied in the device of FIG. 1.

In the embodiment of FIG. 2, the flow channel associated with chamber 250 preferably has a narrow cross-sectional area that is less than a predetermined percentage of the upstream cross-sectional area 224, below which percentage the narrow cross-sectional area is effective to substantially allow air flow and to substantially restrict liquid flow through the vertically oriented flow channel chamber 250. The narrow cross-sectional area of the flow channel associated with chamber 250 preferably is less than 50 percent of the upstream cross-sectional area 224 of the flow channel 210. Likewise, the downstream cross-sectional area 214 is preferably that is at least 50% greater than the upstream crosssectional area 224. With regard to the diagonally-oriented flow channel in each of the above embodiments, this channel is at an angle relative to the vertically-oriented flow channel, which angle is between about 10 degrees and about 80 degrees.

From the above, it may be appreciated that the present invention provides an improvement to aspiration flow control, in configuring first and second flow channels to separate air bubbles from the stream of fluid flow to thereby restrict the passage of air bubbles to an aspiration flow measurement means. The present invention is illustrated herein by example, and various modifications may be made by a person of ordinary skill in the art.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. An air separator in an aspiration flow measurement device for an ophthalmic microsurgical system comprising:
    a flow measurement housing having a diagonally-oriented flow channel and a vertically oriented flow channel that adjoins the diagonally-oriented flow channel at a junction, the diagonally oriented flow channel having an upstream cross-sectional area disposed a predetermined distance upstream of the junction, and a downstream portion disposed downstream of the junction, wherein the downstream portion has a downstream cross-sectional area that is greater than that of the upstream cross-sectional area by a predetermined percentage that is sufficient to cause the velocity of fluid entering the downstream portion to slow down to an extent that air within the downstream portion rises within the downstream portion and escapes into the vertically-oriented flow channel.

2. The air separator of claim 1, wherein the downstream portion has a downstream cross-sectional area that is greater than that of the upstream cross-sectional area by a percentage that is sufficient to increase flow resistance a sufficient extent to cause air bubbles to rise and escape through the vertically-oriented flow channel, to thereby allow the passage of liquid and restrict the passage of air bubbles through the aspiration flow measurement device.

3. The air separator of claim 2, wherein the downstream portion has a cross-sectional area that is at least 50% greater than the upstream cross-sectional area.

4. The air separator of claim 1, wherein the vertically-oriented flow channel has a narrow cross-sectional area that is less than a predetermined percentage of the cross-sectional area of the upstream cross-sectional area, below which percentage the narrow cross-sectional area is effective to substantially allow air flow and to substantially restrict liquid flow through the vertically-oriented flow channel.

5. The air separator of claim 1, wherein the narrow cross-sectional area of the vertically-oriented flow channel is less than 50 percent of the upstream cross-sectional area of the diagonally oriented flow channel.

6. The air separator of claim 1 wherein the diagonally-oriented flow channel is at an angle relative to the vertically-oriented flow channel, which angle is between about 10 degrees and about 80 degrees.

7. The air separator of claim 1, wherein the upstream cross-sectional area is positioned within a predetermined distance of the junction between the diagonally-oriented flow channel and the vertically-oriented flow channel, such that fluid flow through the upstream cross-sectional area is slowed beyond the junction to a separation velocity of which is slower than the velocity of air bubbles rising in the downstream portion.

8. An air separator in an aspiration flow measurement device for an ophthalmic microsurgical system comprising:
a housing having a diagonally-oriented flow channel and a vertically oriented flow channel that adjoins the diagonally-oriented flow channel at a junction, the diagonally-oriented flow channel having an upstream cross-sectional area disposed upstream of the junction, and a downstream portion disposed downstream of the junction, wherein the downstream portion has a cross-sectional area that is greater than that of an upstream cross-sectional area by a predetermined percentage that is sufficient to cause the velocity of fluid entering the downstream portion to slow down, such that air within the downstream portion rises within the flow channel and escapes into the vertically-oriented flow channel.

9. The air separator of claim 8, wherein the downstream portion has a cross-sectional area that is greater than that of the upstream cross-sectional area by a percentage that is sufficient to create an increase in flow resistance sufficient to cause air bubbles to rise and escape through the vertically-oriented flow channel, to thereby allow the passage of liquid and restrict the passage of air bubbles through the surgical cassette.

10. The air separator of claim 9, wherein the cross-sectional area of the downstream portion of the diagonally oriented flow channel is at least 50% greater than the upstream cross-sectional area.

11. The air separator of claim 8, wherein the vertically oriented flow channel has a narrow cross-sectional area that is less than a predetermined percentage of the upstream cross-sectional area of the diagonally oriented flow channel, below which percentage the narrow cross-sectional area is effective to substantially allow air flow and to substantially restrict liquid flow through the vertically-oriented flow channel.

12. The air separator devise of claim 8, wherein the narrow cross-sectional area of the vertically-oriented flow channel is less than 50 percent of the upstream cross-sectional area of the diagonally oriented flow channel.

13. The air separator of claim 8 wherein the diagonally-oriented flow channel is at an angle relative to the vertically-oriented flow channel, which angle is between about 10 degrees and about 80 degrees.

14. The air separator of claim 8, wherein the end of the upstream portion having an upstream cross-sectional area is positioned within a predetermined distance of the junction between the diagonally-oriented flow channel and the vertically-oriented flow channel, such that fluid flow beyond the junction is slowed to a separation velocity that is slower than the velocity of air bubbles rising in the downstream portion.

15. An air separator in an aspiration flow measurement device for an ophthalmic microsurgical system comprising:
a housing having a diagonally-oriented flow channel and a vertically-oriented flow channel adjoining the diagonally-oriented flow channel, the diagonally-oriented flow channel having an upstream cross-sectional area disposed upstream of the flow channel, and having a downstream portion with a cross-sectional area that is greater than that of the upstream portion by a predetermined percentage that is sufficient to cause an increase in flow resistance that reduces the velocity of fluid flow in the downstream portion to an extent that causes air bubbles within the downstream portion to rise and escape into the vertically-oriented flow channel, so as to allow the passage of liquid through the downstream portion and to restrict passage of air bubbles through the downstream portion.

16. The air separator of claim 15, wherein the vertically-oriented flow channel has a narrow cross-sectional area that is less than a predetermined percentage of the upstream cross-sectional area of the diagonally oriented flow channel, below which percentage the narrow cross-sectional area is effective to substantially allow air flow and to substantially restrict liquid flow through the vertically-oriented flow channel.

17. The air separator of claim 15, wherein the cross-sectional area of the downstream portion of the diagonally oriented flow channel is at least 50% greater than the upstream cross-sectional area of the diagonally oriented flow channel.

18. The air separator of claim 15, wherein the end of the upstream portion having an upstream cross-sectional area is positioned within a predetermined distance of the junction point between the diagonally-oriented flow channel and the vertically-oriented flow channel, such that fluid flow beyond the junction is slowed to a separation velocity that is slower than the velocity of air bubbles rising in the downstream portion.

* * * * *